(12) United States Patent
Shreve et al.

(10) Patent No.: US 9,341,277 B2
(45) Date of Patent: May 17, 2016

(54) METHOD, SYSTEM AND APPARATUS FOR AUTOMATIC CALIBRATION OF A NEEDLE VALVE DEVICE IN A PRESSURIZED FLOW SYSTEM

(71) Applicant: Waters Technologies Corporation, Milford, MA (US)

(72) Inventors: Joshua A. Shreve, Franklin, MA (US); Paul Keenan, Harrisville, RI (US); John Maillet, Jr., Hudson, MA (US); Ryan Hill, Watertown, MA (US)

(73) Assignee: Waters Technologies Corporation, Milford, MA (US)

( * ) Notice: Subject to any disclaimer, the term of this patent is extended or adjusted under 35 U.S.C. 154(b) by 67 days.

(21) Appl. No.: 14/381,974

(22) PCT Filed: Mar. 7, 2013

(86) PCT No.: PCT/US2013/029580
§ 371 (c)(1),
(2) Date: Aug. 28, 2014

(87) PCT Pub. No.: WO2013/134496
PCT Pub. Date: Sep. 12, 2013

(65) Prior Publication Data
US 2015/0059864 A1 Mar. 5, 2015

Related U.S. Application Data

(60) Provisional application No. 61/607,930, filed on Mar. 7, 2012.

(51) Int. Cl.
*F16K 27/02* (2006.01)
*F16K 1/38* (2006.01)
(Continued)

(52) U.S. Cl.
CPC . *F16K 27/02* (2013.01); *F16K 1/38* (2013.01); *F16K 31/0655* (2013.01);
(Continued)

(58) Field of Classification Search
CPC ....... F16K 27/02; F16K 1/38; F16K 31/0655; G01N 30/20; G01N 30/32; B01D 15/40
See application file for complete search history.

(56) References Cited

U.S. PATENT DOCUMENTS 3,119,449 A * 1/1964 Price ..................... E21B 34/02
137/382
3,409,271 A * 11/1968 Kallenbach ............... F16K 1/38
251/265

(Continued)

OTHER PUBLICATIONS

Guiochon G, et al., Fundamental challenges and opportunities for preparative supercritical fluid chromatography. J Chromatogr A. Feb. 25, 2011;1218(8):1037-114.

(Continued)

*Primary Examiner* — Craig Schneider
*Assistant Examiner* — Kevin Barss
(74) *Attorney, Agent, or Firm* — McCarter & English, LLP; Deborah M. Vernon

(57) ABSTRACT

Exemplary embodiments are directed to apparatus, systems and methods used in connection with a needle valve device operating in a pressurized flow system. The apparatus, systems and methods provide for automatic positioning of a needle relative to a seat in the needle valve device to provide consistent calibration with minimal user interaction after a maintenance event or upon a start-up of the pressurized flow system. The apparatus, systems and methods utilize a calibration collar secured to a shaft of an actuator within the needle valve device. The calibration collar includes one or more locking mechanism and a spring.

25 Claims, 11 Drawing Sheets

(51) Int. Cl.
  *G01N 30/20* (2006.01)
  *G01N 30/32* (2006.01)
  *F16K 31/06* (2006.01)
  *B01D 15/40* (2006.01)

(52) U.S. Cl.
  CPC .............. *G01N 30/20* (2013.01); *G01N 30/32* (2013.01); *B01D 15/40* (2013.01); *Y10T 137/0486* (2015.04); *Y10T 137/6065* (2015.04)

(56) References Cited

U.S. PATENT DOCUMENTS

| | | | | |
|---|---|---|---|---|
| 3,441,249 | A * | 4/1969 | Wilfred | F16K 47/10 137/556 |
| 4,099,703 | A * | 7/1978 | Lush | F16K 1/52 251/122 |
| 4,462,428 | A * | 7/1984 | Guenther | B05B 12/00 137/868 |
| 4,568,499 | A * | 2/1986 | Wood | F02M 3/10 251/227 |
| 4,575,043 | A * | 3/1986 | Braatz | F16K 1/38 251/122 |
| 4,823,807 | A | 4/1989 | Russell et al. | |
| 5,711,786 | A * | 1/1998 | Hinshaw | G01N 30/16 73/23.25 |
| 5,741,960 | A * | 4/1998 | Payne | G01N 1/2035 422/89 |
| 2005/0284209 | A1 * | 12/2005 | Tipler | G01N 30/12 73/23.42 |
| 2010/0096227 | A1 | 4/2010 | Manuel | |
| 2011/0313397 | A1 | 12/2011 | Gold | |
| 2015/0013803 | A1 * | 1/2015 | Shreve | F17D 3/00 137/624.12 |
| 2015/0014563 | A1 * | 1/2015 | Shreve | G05D 16/2013 251/129.19 |
| 2015/0034168 | A1 * | 2/2015 | Shreve | G01N 30/32 137/14 |
| 2015/0047500 | A1 * | 2/2015 | Shreve | B01D 15/163 95/19 |
| 2015/0083947 | A1 * | 3/2015 | Shreve | F16K 25/005 251/129.15 |

OTHER PUBLICATIONS

International Search Report for PCT/US2013/29580 date of mailing May 8, 2013.

* cited by examiner

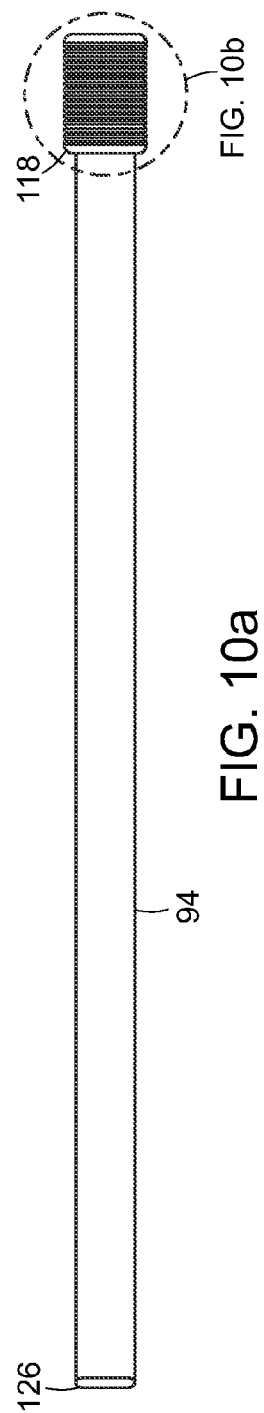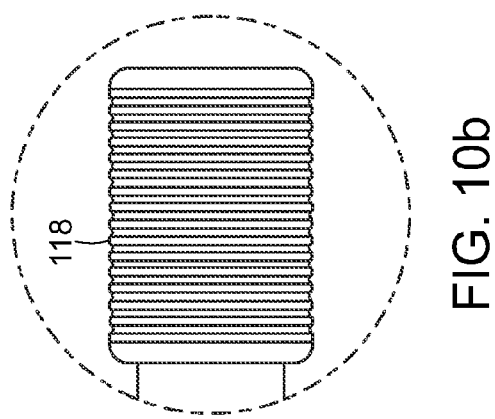

METHOD, SYSTEM AND APPARATUS FOR AUTOMATIC CALIBRATION OF A NEEDLE VALVE DEVICE IN A PRESSURIZED FLOW SYSTEM

RELATED APPLICATIONS

This application is a National Stage Application of International Application No. PCT/US2013/029580, filed Mar. 7, 2013, which claims priority to U.S. Provisional Application No. 61/607,930, filing date Mar. 7, 2012. Each of the foregoing applications is incorporated herein by reference in its entirety.

TECHNICAL FIELD

The present disclosure relates to needle valve devices and associated apparatus, systems and methods and, in particular, to needle valve devices and associated apparatus, systems and methods that allow for automatic calibration of a position of a needle within a needle valve device used in a pressurized flow application, such as, for example $CO_2$-based chromatography.

BACKGROUND

Chromatographic techniques are important tools for the identification and separation of complex samples. The basic principle underlying chromatographic techniques is the separation of a mixture into individual components by transporting the mixture in a moving fluid through a retentive media. The moving fluid is typically referred to as the mobile phase and the retentive media is typically referred to as the stationary phase. The separation of the various constituents of the mixture is based on differential partitioning between the mobile and stationary phases. Differences in components' partition coefficient result in differential retention on the stationary phase, resulting in separation.

Conventionally, the methods of choice for chromatographic separations have been gas chromatography (GC) and liquid chromatography (LC). One major difference between GC and LC is that the mobile phase in GC is a gas, whereas the mobile phase in LC is a liquid. For example, in GC, a supply of inert carrier gas (mobile phase) is continually passed as a stream through a heated column containing porous sorptive media (stationary phase). A sample of the subject mixture is injected into the mobile phase stream and passed through the column, where separation of the mixture is primarily due to the differences in the volatile characteristics of each sample component at the temperature of the column. A detector, positioned at the outlet end of the column, detects each of the separated components as they exit the column. Although GC is typically a sensitive method of analysis, the high temperatures required in GC make this method unsuitable for high molecular weight biopolymers or proteins (heat will denature them), frequently encountered in biochemistry.

Conversely, LC is a separation technique in which the mobile phase is a liquid and does not require volatilization of the sample. Liquid chromatography that generally utilizes small packing particles and moderately high pressure is referred to as high-performance liquid chromatography (HPLC); whereas liquid chromatography that generally utilizes very small packing particles and high pressure is referred to as ultra-high performance liquid chromatography (UHPLC). In HPLC and UHPLC the sample is forced by a liquid at high pressure (the mobile phase) through a column that is packed with a stationary phase composed of irregularly or spherically shaped particles, a porous monolithic layer, or a porous membrane.

Because LC uses liquid as the mobile phase, LC techniques are capable of analyzing higher molecular weight compounds and, in some cases, LC can be used to prepare large scale batches of purified protein(s). However, in contrast, GC techniques are typically more sensitive and readily allow for the separation of single chiral materials. Thus, GC has conventionally been used to isolate and determine the relative purity of a chiral compound, e.g., by determining the enantiomeric excess (% ee) or the diastereomeric excess (% de) of a particular sample. As with most chromatographic techniques, the limiting factor in both GC and LC has been the ability to obtain and/or reproduce pure sample separations, each of which are typically dependent on the apparatus, methods, and conditions employed, e.g., flow rate, column size, column packing material, solvent gradient, etc.

Supercritical Fluid Chromatography is another chromatographic technique, which has typically been used in preparative applications. For every liquid substance there is a temperature above which it can no longer exist as a liquid, no matter how much pressure is applied. Likewise, there is a pressure above which the substance can no longer exist as a gas no matter how much the temperature is raised. These points are called the supercritical temperature and supercritical pressure, and define the boundaries on a phase diagram for a pure substance (FIG. 1). At this point, the liquid and vapor have the same density and the fluid cannot be liquefied by increasing the pressure. Above this point, where no phase change occurs, the substance acts as a supercritical fluid (SF). Thus, SF can be described as a fluid obtained by heating above the critical temperature and compressing above the critical pressure. There is a continuous transition from liquid to SF by increasing temperature at constant pressure or from gas to SF by increasing pressure at constant temperature.

The term SFC, while typically standing for Supercritical Fluid Chromatography, does not require or mean that supercritical conditions are obtained during or maintained throughout the separation. That is, columns do not have to be always operated in the critical region of the mobile phase. For example, in the event that the mobile phase includes a modifier (e.g., $CO_2$ and methanol as a modifier), the mobile phase is often in its subcritical region (e.g., a highly compressed gas or a compressible liquid rather than a supercritical fluid). In fact, as Guiochon et al note in section 2.3 of their review article entitled "Fundamental challenges and opportunities for preparative supercritical fluid chromatography" Journal of Chromatography A, 1218 (2011) 1037-1114: "It is obvious that SFC has very often been and still is run under subcritical conditions." Thus, the term SFC is not limited to processes requiring supercritical conditions.

Because SFC typically uses $CO_2$, SFC processes are inexpensive, innocuous, eco-friendly, and non-toxic. There is typically no need for the use of volatile solvent(s) (e.g., hexane). Finally, the mobile phase in SFC processes (e.g., $CO_2$ together with any modifier/additive as a SF, highly compressed gas, or compressible liquid) typically have higher diffusion constants and lower viscosities relative to liquid solvents. The low viscosity means that pressure drops across the column for a given flow rate is greatly reduced. The increased diffusivity means longer column length can be used.

SUMMARY

Exemplary embodiments of the present technology are directed to apparatus, systems and methods for automatically setting a position of a needle in a needle valve device used in a pressurized flow system. Needles and/or their associated seats in pressurized flow systems can wear out over time and can require replacement or reconfiguration for a different application. Due to tolerances needed for adequate pressure control, the positioning of the needle relative to the seat is generally calibrated after a maintenance event or prior to a start-up condition. In embodiments of the present technology, mechanical means, such as, for example, springs and locking mechanisms are utilized to automatically set (e.g., mechanically set) the position of the needle in a needle valve device. As a result, little or no interaction from a user is needed to calibrate a needle valve device upon start-up and/or after maintenance of the needle valve device. Embodiments of the needle valve device include pressure regulators in pressurized flow systems. Embodiments of the pressurized flow system can be implemented as a $CO_2$-based chromatography system in which the mobile phase is passed through a stationary phase and sample components of a sample injected into the mobile phase are separated and one or more characteristics of the sample components are detected.

In accordance with embodiments of the present disclosure, calibration collars or apparatus for automatically setting a position of a needle to a seat in a pressurized flow system including an actuator positioned to drive the needle relative to the seat are disclosed. The actuator includes a shaft including an exterior liner and an interior extendable section. The calibration collar includes a housing, a first securing mechanism, a second securing mechanism, and a spring. The housing of the calibration collar includes a first end and a second end and the housing defines a channel sized to accept at least a portion of the shaft of the actuator. The first securing mechanism of the calibration collar is positioned at the second end of the housing and surrounds the channel. The first securing mechanism, when in a locked position, holds the housing to the exterior liner of the shaft. The second securing mechanism is independent of the first securing mechanism. The second securing mechanism, when in a closed position, grips at least a portion of an external perimeter surface of the interior extendable section of the shaft to clamp the housing to the shaft. The spring of the calibration collar is disposed at least partially in the first end of the housing and extends into the channel to apply a known load on the shaft when the shaft is seated in the housing.

Embodiments of the above exemplary calibration collars or apparatus can include one or more of the following features. In some embodiments, the second securing mechanism is positioned between the first securing mechanism and the first end of the housing. In embodiments, the first and/or second securing mechanism is a clamp. In certain embodiments, the first securing mechanism and/or the second securing mechanism clamp includes a base portion integrally formed with the housing and a top portion secured to the base portion with two fasteners, e.g., screws. In some embodiments, the second securing mechanism clamp includes a first portion integrally formed with the housing and having a first free end and a second portion also integrally formed with the housing and having a second free end, wherein the second free end is opposite of the first free end and the first and second portions are secured together with a fastener. The housing can be formed of metal. In some embodiments, the housing is formed at least in part of stainless steel. In other embodiments, the housing is formed at least in part of aluminum. Other metals, alloys and combinations of materials are also possible. Embodiments can also include a textured housing for facilitating gripping between the actuator shaft and the calibration collar. For example, one or more embodiments include a surface (or at least a portion of a surface) of the housing defining the channel with a texture applied. The textured surface facilitates gripping of at least a portion of an external perimeter surface of the interior extendable section of the shaft of the actuator when the second securing mechanism is in a closed position. The texture applied to the surface or at least portion of the surface of the housing can include one or more of radial grooves, raised bumps, or raised ribs. In embodiments, the second securing mechanism is an electromechanical locking assembly. The electromechanical locking assembly can automatically place the second securing mechanism in the closed position upon start-up of the device and/or after a maintenance event.

In accordance with embodiments of the present technology, systems including the calibration collar attached to an actuator shaft of a needle valve device are disclosed. The calibration collar includes one or more locking mechanisms and a spring to mechanically position the needle of the needle valve device in relation to the seat with little to no interaction from a user. In some embodiments, the calibration collar is implemented as the calibration collar described above. The system can be used in a pressurized flow application, such as, for example, $CO_2$-based chromatography and provides consistent calibration of the needle to the seat at each start-up event.

In accordance with embodiments of the present technology, exemplary methods of replacing at least one of a needle or seat in a pressurized flow device are disclosed. Embodiments of the exemplary methods include a number of steps. First, the method includes providing a calibration collar (e.g., one of the exemplary calibration collars described herein) with the first securing mechanism in the locked position and the second securing mechanism in the closed position to secure and grip the calibration collar to the shaft of the actuator in an operating position in which the needle and the seat are in a calibrated position. Next, the method includes moving the second securing mechanism from the closed position to the open position to release the grip of the calibration collar from the interior extendable section of the shaft. The method also includes moving the shaft to obtain access to the needle, replacing at least one of the needle or seat; and positioning the shaft to be in physical contact with an end of the needle or a replacement needle. Once the shaft is in physical contact with the needle (or replacement needle), the method includes the step of moving the second securing mechanism from the open position to the closed position to grip the interior extendable section of the shaft and position the replaced needle or seat in the calibrated position.

Embodiments of the above exemplary methods can include one or more of the following features. In some embodiments, moving the second securing mechanism from the closed to the open position includes releasing a clamping mechanism, such as, for example loosening a fastener or electromechanically releasing an electromechanical clamp. In embodiments, moving the second securing mechanism from the open position to the closed position includes activating a clamping mechanism, such as, for example, tightening a fastener or activating an electromechanical clamp to close. In some embodiments, electromechanically releasing or activating of the second securing mechanism occurs automatically (e.g., without user interaction). In embodiments, the electromechanically activating the second securing mechanism occurs automatically upon a start-up condition.

In accordance with embodiments of the present technology, exemplary methods of setting and maintaining a calibrated position between a needle and a seat in a pressurized flow system are disclosed. In general, the pressurized flow system can be any type of pressurized flow system, such as, for example, a $CO_2$-based chromatography system. In addition, the pressurized flow system includes an actuator positioned to drive the needle relative to the seat. Embodiments of these exemplary methods include placing the calibration collar (e.g., one of the exemplary calibration collars described herein) on a first end of the shaft of the actuator such that the channel defined in the housing of the calibration collar at least partially surrounds an end portion of the shaft. The methods also include a step of securing the first securing mechanism of the calibration collar to the shaft to hold the housing to the shaft and to position the first securing mechanism in the locked position. The methods further include a step of positioning the needle relative to the seat to set the calibrated position. The methods also include a step of positioning a second end of the shaft of the actuator to be in physical contact with an exposed end of the needle; and securing the second securing mechanism of the calibration collar to the shaft to grip the external perimeter surface of the extendable section of the shaft to maintain the calibrated position and to position the second securing mechanism in the closed position.

Embodiments of the above exemplary methods can include additional features. For example, embodiments can include additional steps in which the grip of the calibration collar is released so that the shaft of the actuator can be displaced (e.g., shaft moved for maintenance purposes, such as, for example, replacement of needle or seat) without the need for recalibration. For example, methods can further include moving the second securing mechanism from the closed position to the open position to release the grip of the calibration collar from the shaft; moving the second end of the shaft to obtain access to the needle (e.g., obtain access to the needle for maintenance/replacement purposes); positioning the second end of the shaft to be in physical contact with the exposed end of the needle (e.g., reposition shaft after completing maintenance/replacement); and moving the second securing mechanism from the open position to the closed position to grip the shaft and to return the needle and the seat to the calibrated position.

The exemplary apparatus, calibration collars, systems, and methods of the present disclosure provide numerous advantages. For example, by incorporating one or more of the exemplary apparatus, calibration collars, systems or methods of the present disclosure into a pressurized flow system including a needle valve device, consistent needle calibration is achieved at, for example, start-up and/or after maintenance events. Consistent needle calibration allows for consistent behavior, which ultimately provides better separation results in chromatographic applications. In addition to providing consistent calibration, the exemplary apparatus, calibration collars, systems and methods provide increases in efficiency and minimization of maintenance time. That is, the apparatus, calibration collars, systems and methods provide an automatic or mechanically self-calibrating needle valve that simplifies maintenance events by limiting or eliminating user interaction (e.g., minimizes or eliminates decisions or calibration positioning by the user or controlling software) to recalibrate the position of the needle relative to the seat in the field after maintenance events.

BRIEF DESCRIPTION OF THE DRAWINGS

The foregoing and other features and advantages provided by the present disclosure will be more fully understood from the following description of exemplary embodiments when read together with the accompanying drawings, in which:

FIGS. 10(a)-(b) are side and detailed views of an exemplary embodiment of an interior portion of a shaft of an actuator included in the pressure regulator shown in FIG. 6;

DESCRIPTION OF EXEMPLARY EMBODIMENT

Figure 1:
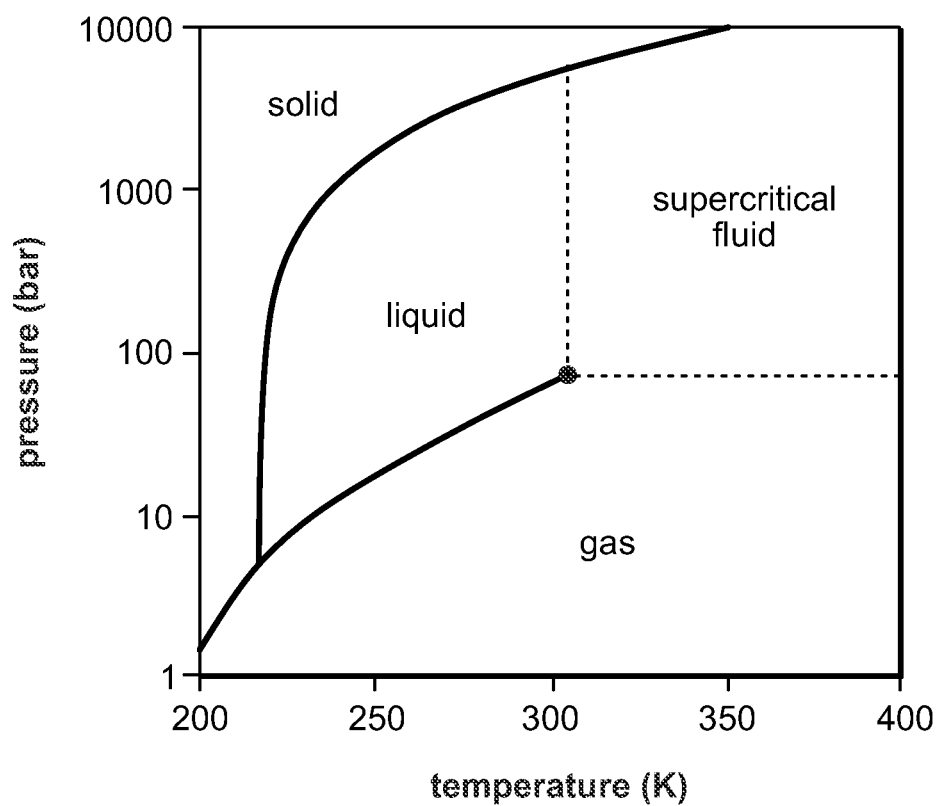
FIG. 1 is an exemplary graph of the physical state of a substance in relation to a temperature and pressure associated with the substance.

SFC can be adapted as a hybrid between HPLC and GC apparatuses, where the predominant modification is replacement of either the liquid or gas mobile phase with a supercritical fluid (or near supercritical fluid) mobile phase, such as with $CO_2$. In SFC, the mobile phase is initially pumped as a liquid or gas and is brought into the supercritical region by heating or pressurizing the mobile phase above its supercritical temperature/pressure prior to entry into a column. As the mobile phase passes through an injection valve, the sample is introduced into the supercritical stream, and the mixture is then transferred into a column. The mixture passes through the column (at supercritical or liquid state) and into the detector.

In general, the mobile phase in SFC processes have the ability to act both as substance carriers (like the mobile phases in GC), and dissolve substances readily (like the solvents used in LC). In addition to generally having lower viscosities and better diffusion profiles similar to those of certain gases, the mobile phase in SFC processes also generally have high densities and dissolving capacities similar to those of certain liquids. For example, SFs' high densities (0.2-0.5 $gm/cm^3$) provide for their remarkable ability to dissolve large, non-volatile molecules, e.g., supercritical or near supercritical $CO_2$ readily dissolves n-alkanes, di-n-alkyl phthalates, and polycyclic and aromatic compounds. Since the diffusion of solutes in a SFC mobile phase is about ten times greater than that in liquids (about three times less than in gases), this results in a decrease in resistance to mass transfer in the column and allows for fast high resolution separation. Also, the solvation strength of the mobile phase in SFC processes is directly related to the fluid density. Thus, the solubility of solids can be easily manipulated by making slight changes in temperatures and pressures.

Another important property of the mobile phase in SFC processes is that it provides high resolution chromatography at much lower temperatures. For example, an analyte dissolved in supercritical $CO_2$ can be recovered by reducing the pressure and allowing the sample to evaporate under ambient laboratory conditions. This property is useful when dealing with thermally unstable analytes, such as high molecular weight biopolymers or proteins.

The combination of one or more mechanical or column changes to an SFC instrument (e.g., a $CO_2$-based chromatography instrument) coupled with the inherent properties of the SFC itself, allows for the separation of both chiral and achiral compounds, and has become increasingly predominant in the field of preparatory separations for drug discovery and development. Despite considerable advances in SFC technology, there is a need to develop innovative methods and apparatuses that improve the use of SFC. Controlling and stabilizing the pressure in an SFC instrument by one or more process and/or improving one or more of the instrumental characteristics of the system, may lead to, amongst others, improved compound separation and efficiency.

For example, better resolution and increased flow rate would decrease cycle times (i.e., shorter cycle times) and allow for improved separation of both chiral and achiral compounds, and lead to an overall increase in laboratory efficiency; increased speed and throughput would decrease the amount of solvent and cost(s) associated with SFC; and the ability to further integrate SFC with other detection methods, such as Mass Spectrometry (MS), Flame Ionization Detectors (FID), and Ultraviolet/Visible (UV) detectors, would improve the mainstream use of SFC using a mobile phase including $CO_2$ as an eco-friendly, yet effective, alternative method for the fast, complete, and sensitive analysis of analytes.

Exemplary embodiments of the present disclosure are directed to automatically setting a position of a needle in a needle valve device used in a pressurized flow system, such as, for example a $CO_2$-based chromatography system. Exemplary embodiments can implement one or more apparatus, systems or methods for setting the position of a needle relative to a seat in a needle valve device to provide consistent calibration with minimal user interaction after a maintenance event or upon a start-up of the pressurized flow system (e.g., calibration of the needle valve device in the field after a maintenance event). As an example, in one embodiment, a user performing maintenance on the needle valve device merely needs to open one of two securing mechanisms on a calibration collar attached to the shaft of an actuator to access the needle. To provide consistent calibration and to place the needle back into a calibrated position with a seat after maintenance, the user merely has to place the shaft in physical contact with the needle and close the securing mechanism. That is, the user does not have to recalibrate the position of the needle to the seat through the use of manual or computer-assisted calibration techniques, rather the mechanical collar locked to the shaft returns the needle to the calibrated position automatically (e.g., self calibration).

As used herein, the terms "downstream" and "upstream" refer to relative locations in a system flow, wherein upstream refers to being associated with an earlier portion of the system flow compared to later portion of the system flow and downstream refers to being associated with a later portion of the system flow compared to an earlier portion of the system flow.

Figure 2:
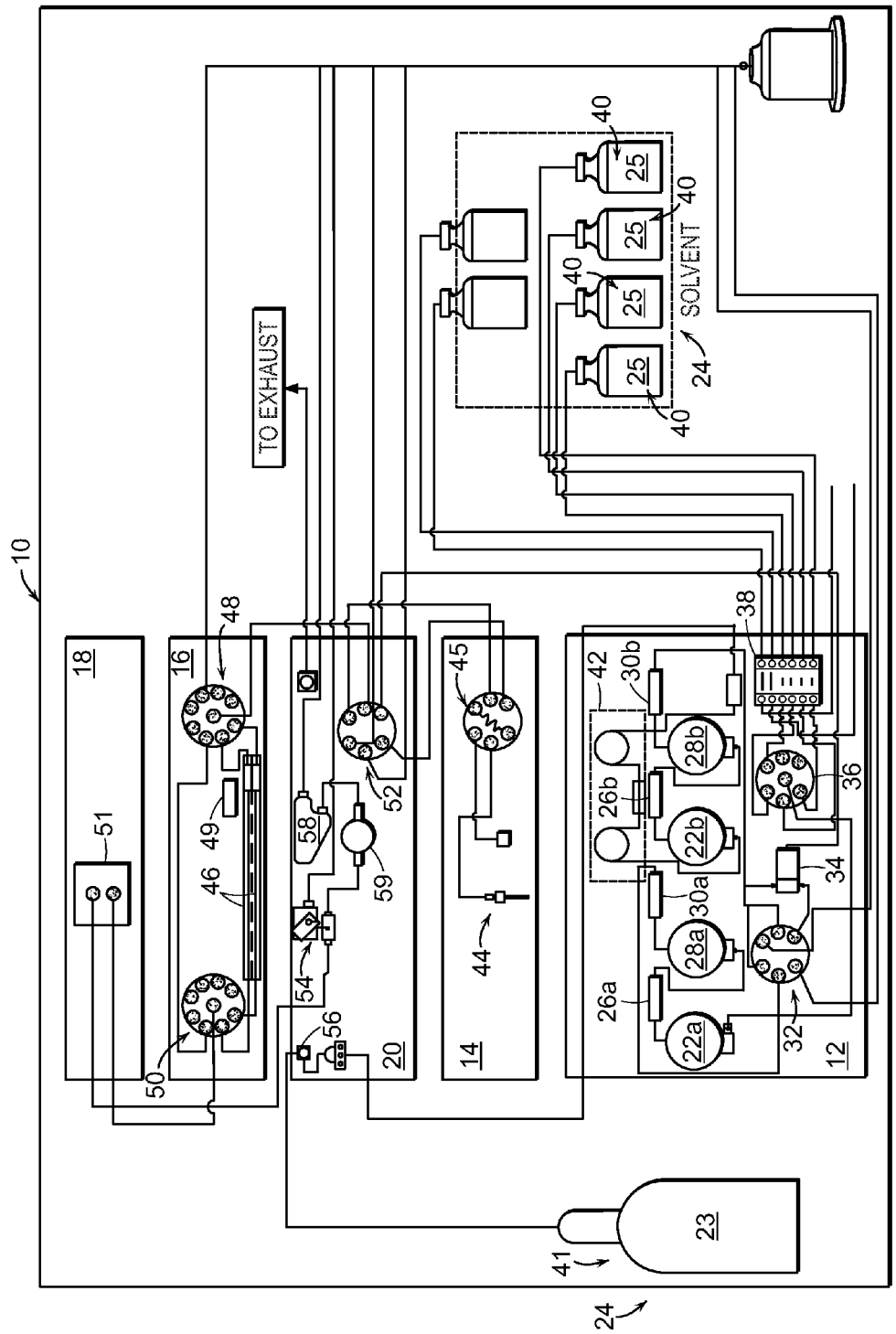
FIG. 2 is a block diagram of an exemplary pressurized flow system.

FIG. 2 is a block diagram of an exemplary pressurized flow system, which in the present embodiment is implemented as a $CO_2$-based chromatography system 10 (hereinafter "system 10"). While the present embodiment is illustrative of a $CO_2$-based chromatography system operated at or near supercritical conditions, those skilled in the art will recognize that exemplary embodiments of the present disclosure can be implemented as other pressurized flow systems and that one or more system components of the present disclosure can be implemented as components of other pressurized systems. System 10 can be configured to detect sample components of a sample using chromatographic separation in which the sample is introduced into a mobile phase that is passed through a stationary phase. System 10 can include one or more system components for managing and/or facilitating control of the physical state of the mobile phase, control of the pressure of system 10, introduction of the sample to the mobile phase, separation of the sample into components, and/or detection of the sample components, as well as venting of the sample and/or mobile phase from system 10.

Figure 3:
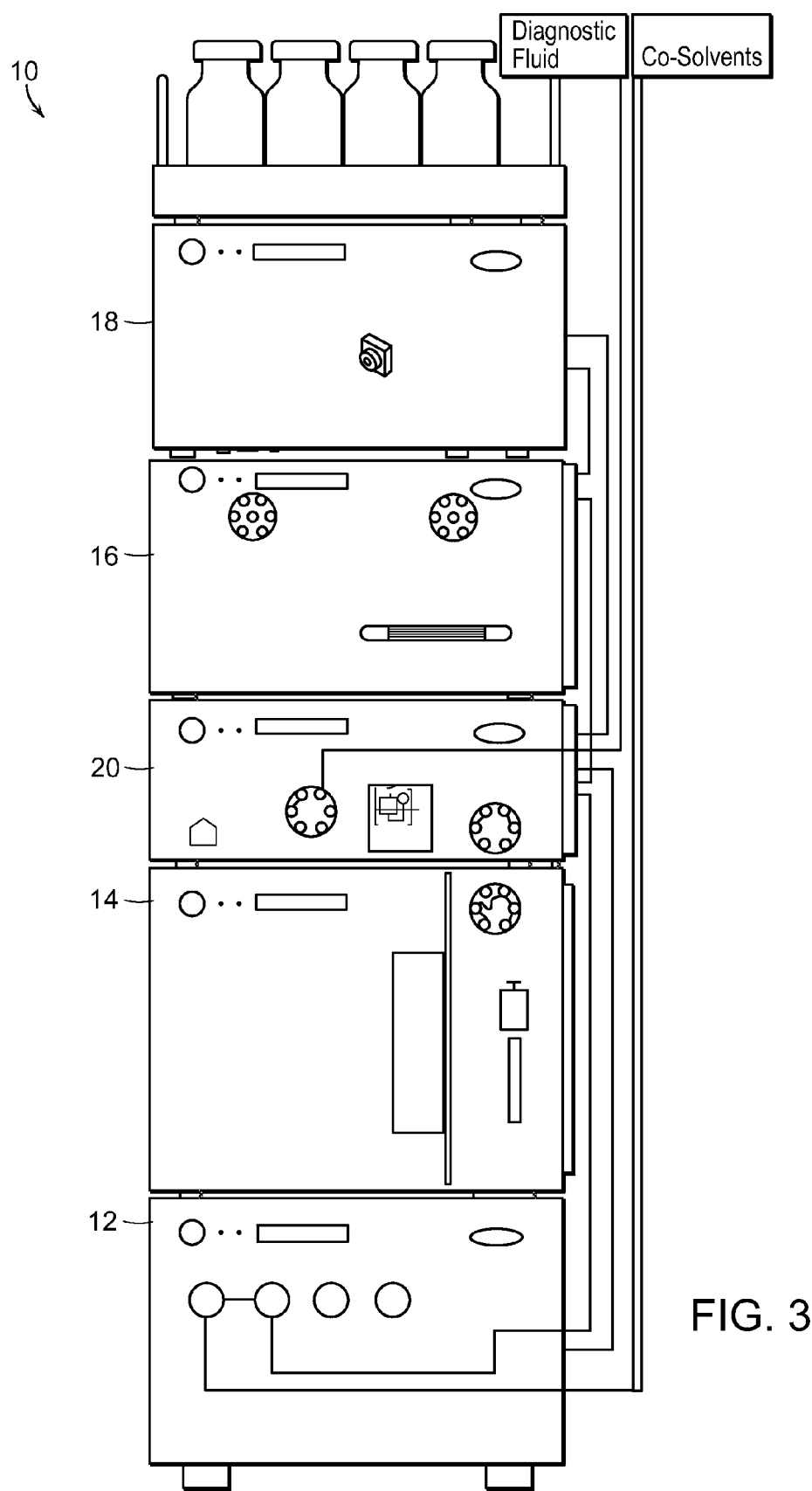
FIG. 3 is a block diagram of an exemplary arrangement of an embodiment of the system of FIG. 2.
Figure 4:
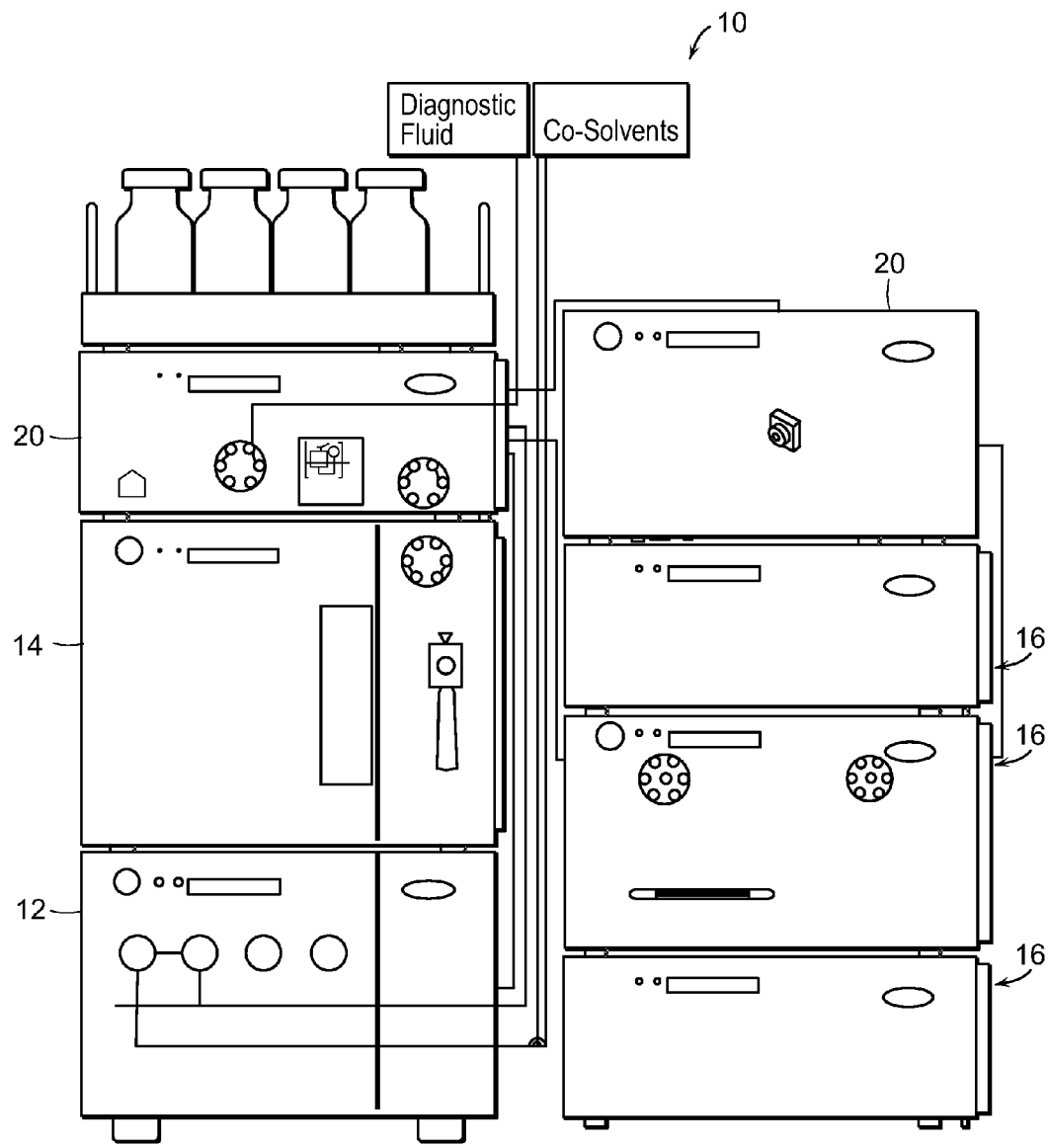
FIG. 4 is a block diagram of another exemplary arrangement of an embodiment of the system of FIG. 2.

In the present embodiment, system 10 can include a solvent delivery system 12, a sample delivery system 14, a sample separation system 16, a detection system 18 (e.g., a PDA detector), and a system/convergence manager 20. In some embodiments, the system components can be arranged in one or more stacks. As another example, in one embodiment, the system components of system 10 can be arranged in a single vertical stack (FIG. 3). The system components of the system 10 can be arranged in multiple stacks (FIG. 4). Those skilled in the art will recognize that other arrangements of the components of system 10 are possible. Furthermore, while embodiments of system 10 have been illustrated as including system components 12, 14, 16, 18, and 20, those skilled in the art will recognize that embodiments of system 10 can be implemented as a single integral unit, that one or more components can be combined, and/or that other configurations are possible.

The solvent delivery system 12 can include one or more pumps 22a and 22b configured to pump one or more solvents 24, such as mobile phase media 23 (e.g., carbon dioxide) and/or modifier media 25 (i.e., a co-solvent, such as e.g., methanol, ethanol, 2-methoxyethanol, isopropyl alcohol, or dioxane), through the system 10 at a predetermined flow rate. For example, the pump 22a can be in pumping communication with the modifier media 25 to pump the modifier media 25 through the system 10, and the pump 22b can be in pumping communication with the mobile phase media 23 to pump the mobile phase media 23 through the system 10. An output of the pump 22a can be monitored by a transducer 26a and an output of the pump 22b can be monitored by a transducer 26b. The transducers 26a and 26b can be configured to sense the pressure and/or flow rate associated with the output of the solvent 24 from the pumps 22a and 22b, respectively. Each pump 22a and/or 22b further includes a pump control valve configured to be actuated into, e.g., a flow position, a block position, a vent position, and the like.

The outputs of the pumps 22a and 22b can be operatively coupled to an input of accumulators 28a and 28b, respectively. The accumulators 28a and 28b are refilled by the outputs of the pumps 22a and 22b, respectively, and can contain an algorithm to reduce undesired fluctuations in the flow rate and/or pressure downstream of the pumps 22a and 22b, which can cause detection noise and/or analysis errors on the system 10. An output of the accumulator 28a can be monitored by a transducer 30a and an output of the accumulator 28b can be monitored by a transducer 30b. The transducers 30a and 30b can be configured to sense pressure and/or flow rate at an output of the accumulators 28a and 28b, respectively. The outputs of the accumulators 28a and 28b can be operatively coupled to a multiport valve 32, which can be controlled to vent the solvent 24 (e.g., mobile phase media 23 and modifier media 25) being pumped by the pumps 22a and 22b and/or to output the solvent 24 to a mixer 34. The mixer 34 can mix the modifier media 25 and the mobile phase media 23 output from the pumps 22a and 22b, respectively (e.g., after first passing through the accumulators 28a and 28b) and can output a mixture of the mobile phase media 23 and the modifier media 25 to form a solvent stream (i.e., mobile phase) that flows through the system 10. The output of the mixer 34 can be operatively coupled to the system/convergence manager 20 as discussed in more detail below.

In exemplary embodiments, the solvent delivery system 12 can include a multiport solvent selection valve 36 and/or a degasser 38. The solvent selection valve 36 and/or the degasser 38 can be operatively disposed between an input of the pump 22a and solvent containers 40 such that the solvent selection valve 36 and/or the degasser 38 are positioned upstream of the pump 22a. The solvent selection valve 36 can be controlled to select the modifier media 23 to be used by the system 10 from one or more solvent containers 40 and the degasser 38 can be configured to remove dissolved gases from the media modifier 23 before the media modifier 23 is pumped through the system 10.

In exemplary embodiments, the solvent delivery system 12 can include a pre-chiller 42 disposed between an input of the pump 22b and a solvent container 41 such that the pre-chiller is disposed upstream of the input to the pump 22b and downstream of the solvent container 41. The pre-chiller 42 can reduced the temperature of the mobile phase media 23 before it is pumped through the system 10 via the pump 22b. In the present embodiment, the mobile phase media 23 can be carbon dioxide. The pre-chiller can decrease the temperature of the carbon dioxide so that the carbon dioxide is maintained in a liquid state (i.e., not a gaseous state) as it is pumped through at least a portion of the system 10. Maintaining the carbon dioxide in a liquid state can facilitate effective metering of the carbon dioxide through the system 10 at the specified flow rate.

The pumps 22a and 22b can pump the solvent 24 through the system 10 to pressurize the system 10 to a specified pressure, which may be controlled, at least in part, by the system/convergence manager 20. In exemplary embodiments, the system 10 can be pressurized to a pressure between about 700 psi and about 18,000 psi or about 1,400 psi and about 8,000 psi. In one embodiment, the system 10 can be pressurized to a pressure of about 6,000 psi. By pressurizing the system 10 at these pressure levels (such as those pressure levels described above), the solvent stream (i.e., mobile phase) can be maintained in a liquid state before transitioning to a supercritical fluid state or near supercritical state (e.g., highly-compressed gas or compressible liquid) for a chromatographic separation in a column, which can be accomplished by raising the temperature of the pressurized solvent stream.

The sample delivery system 14 can select one or more samples to be passed through the system 10 for chromatographic separation and detection. The sample delivery system 14 can include a sample selection and injection member 44 and a multi-port valve 45. The sample selection and injection member 44 can include a needle through which the sample can be injected into the system 10. The multiport valve 45 can be configured to operatively couple the sample selection and injection member 44 to an input port of the system/convergence manager 20.

The sample separation system 16 can receive the sample to be separated and detected from the sample delivery system 14, as well as the pressurized solvent stream from the solvent delivery system 12, and can separate components of the sample passing through the system 10 to facilitate detection of the samples using the detection system 18. The sample separation system 16 can include one or more columns 46 disposed between an inlet valve 48 and an outlet valve 50. The one or more columns 46 can have a generally cylindrical shape that forms a cavity, although one skilled in the art will recognize that other shapes and configurations of the one or more columns is possible. The cavity of the columns 46 can have a volume that can at least partially be filled with retentive media, such as hydrolyzed silica, such as $C_8$ or $C_{18}$, or any hydrocarbon to form the stationary phase of the system 10 and to promote separation of the components of the sample. The inlet valve 48 can be disposed upstream of the one or more columns can be configured to select which of the one or more columns 46, if any, receives the sample. The outlet valve 50 can be disposed downstream of the one or more columns 46 to selectively receive an output from the one or more columns 46 and to pass the output of the selected one or more columns 46 to the detection system 18. The columns 46 can be removably disposed between the valves 48 and 50 to facilitate replacement of the one or more columns 46 to new columns after use. In some embodiments, multiple sample separation systems 16 can be included in the system 10 to provide an expanded quantity of columns 46 available for use by the system 10 (FIG. 4).

In exemplary embodiments, the sample separation system 16 can include a heater 49 to heat the pressurized solvent stream 24 prior and/or while the pressured solvent stream 24 passes through the one or more columns 46. The heater 49 can heat the pressurized solvent stream to a temperature at which the pressured solvent transitions from a liquid state to a supercritical fluid state so that the pressurized solvent stream passes through the one or more columns 46 as a supercritical fluid.

Referring again to FIG. 2, the detection system 18 can be configured to receive components separated from a sample by the one or more columns 46 and to detect a composition of the components for subsequent analysis. In an exemplary embodiment the detection system 18 can include one or more detectors 51 configured to sense one of more characteristics of the sample components. For example, in one embodiment, the detectors 51 can be implemented as one or more photodiode arrays.

The system/convergence manager 20 can be configured to introduce a sample from the sample delivery system 14 into the pressurized solvent stream flowing from the solvent delivery system 12 and to pass the solvent stream and sample to the sample separation system 16. In the present embodiment, the system/convergence manager 20 can include a multiport auxiliary valve 52 which receives the sample injected by the sample delivery system 14 through a first inlet port and the pressurized solvent stream from the solvent delivery system 12 through a second inlet port. The auxiliary valve 52 can mix the sample and the solvent stream and output the sample and solvent stream via an outlet port of the multiport auxiliary valve 52 to an inlet port of the inlet valve 48 of the sample separation system 16.

The system/convergence manager 20 can also be configured to control the pressure of the system 10 and to facilitate cooling, heating, and/or venting of the solvent from the system 10, and can include a vent valve 54, a shut off valve 56, a back pressure regulator 58, and a transducer 59. The vent valve 54 can be disposed downstream of the detection system 18 can be configured to decompress the system 10 by venting the solvent from the system 10 after the solvent has passed through the system 10. The shut-off valve 56 can be configured to disconnect the solvent supply from the inlet of the pump 22b of the solvent delivery system to prevent the solvent from being pumped through the system 10. An exemplary vent valve 54 will be described in more detail below.

The back pressure regulator 58 can control the back pressure of the $CO_2$-based chromatography system 10 to control the flow of the mobile phase and sample through the column, to maintain the mobile phase in the supercritical fluid state (or, in some embodiments, in a near supercritical state, such as, a highly-compressed gas or compressible liquid) as the mobile phase passes through the one or more columns 46 of the sample separation system 16, and/or to prevent the back pressure from forcing the mobile phase reversing its direction a flow through the one or more columns 46. Embodiments of the back pressure regulator 58 can be configured to regulate the pressure of the system 10 so that the physical state of the solvent stream (i.e., mobile phase) does not change uncontrollably upstream of and/or within the back pressure regulator 58. The transducer 59 can be a pressure sensor disposed upstream of the back pressure regulator 58 to sense a pressure of the system 10. The transducer 59 can output a feedback signal to a processing device which can process the signal to control an output of an actuator control signal from the processing device.

Figure 5:
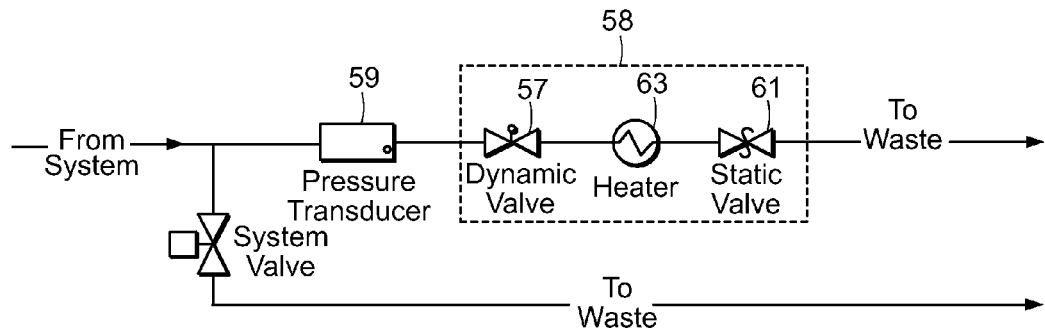
FIG. 5 is a flow diagram of a mobile phase through a system manager portion of the an exemplary embodiment of the pressurized flow system.

In exemplary embodiments, as shown in FIG. 5, the back pressure regulator 58 can include a dynamic pressure regulator 57, a static pressure regulator 61, and a heater 63. The static pressure regulator 61 can be configured to maintain a predetermined pressure upstream of the back pressure regulator 58. The dynamic pressure regulator 57 can be disposed upstream of the static pressure regulator 61 and can be configured to set the system pressure above the predetermined pressure maintained by the static regulator 61. The heater 63 can be disposed downstream of the dynamic pressure regulator 57 and can be disposed in close proximity to the static pressure regulator 61 to heat the solvent stream as it passes through the static pressure regulator 61 to aid in control of the physical state of the solvent as it passes through the static pressure regulator.

In summary, an exemplary operation of the $CO_2$-based chromatography system 10 can pump mobile phase media 23 and modifier media 25 at a specified flow rate through the system 10 as a solvent stream (i.e., mobile phase) and can pressurize the system 10 to a specified pressure so that the solvent stream maintains a liquid state before entering the sample separation system 16. A sample can be injected into the pressurized solvent stream by the sample delivery system 14, and the sample being carried by the pressurized solvent stream can pass through the sample separation system 16, which can heat the pressurized solvent stream to transition the pressurized solvent stream from a liquid state to a supercritical fluid state. The sample and the supercritical fluid solvent stream can pass through at least one of the one or more columns 46 in the sample separation system 16 and the column(s) 46 can separate components of the sample from each other. The separated components can pass the separated components to the detection system 18, which can detect one or more characteristics of the sample for subsequent analysis.

After the separated sample and solvent pass through the detection system 18, the solvent and the sample can be vented from the system 10 by the system/convergence manager 20.

In other embodiments, the system 10 described herein can also be used for preparatory methods and separations. Typical parameters, such as those described above, may be manipulated to achieve effective preparatory separations. For example, the system 10 described herein confers the benefit of exerting higher flow rates, larger columns, and column packing size, each of which contributes to achieving preparatory separation and function, while maintaining little or no variability in overall peak shape, peak size, and/or retention time(s) when compared to respective analytical methods and separations thereof. Thus, in one embodiment, the present disclosure provides $CO_2$-based chromatography systems which are amendable to preparatory methods and separations with high efficiency and correlation to analytical runs.

Figure 6:
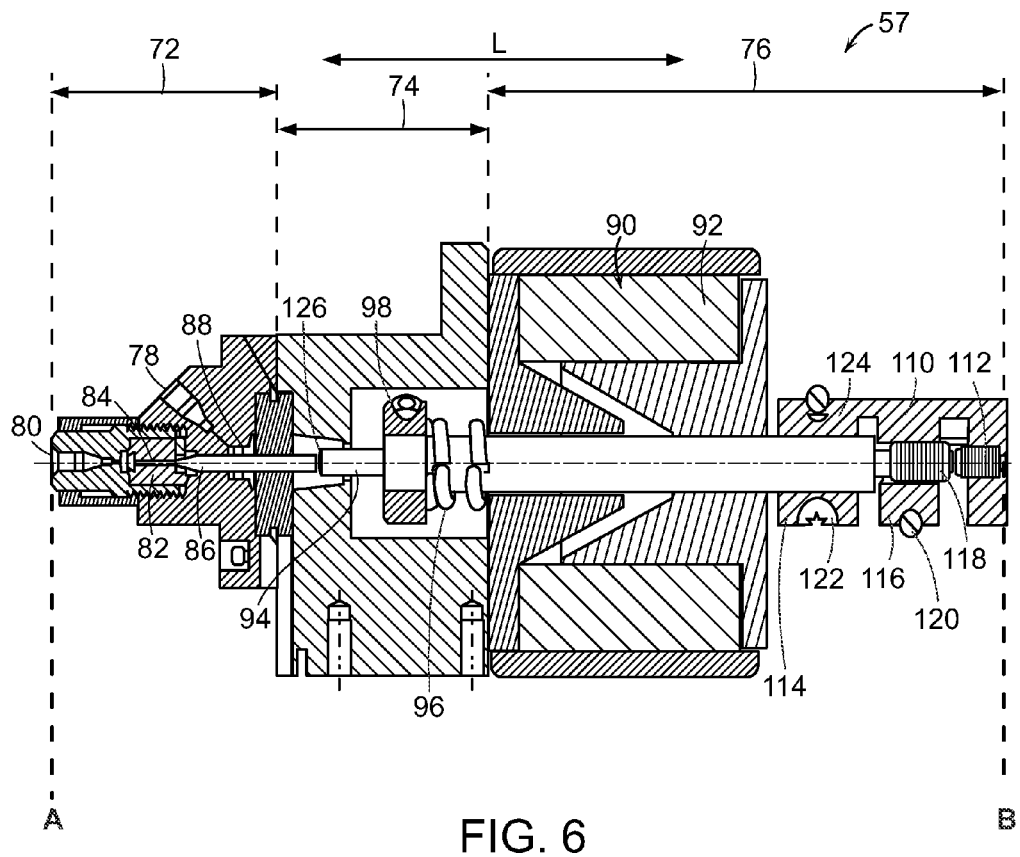
FIG. 6 is a cross-sectional view of a valve assembly for an exemplary dynamic pressure regulator in an exemplary embodiment of the pressurized system.

FIG. 6 is a cross-sectional view of an exemplary embodiment of a dynamic pressure regulator 57 along a longitudinal axis L of the dynamic pressure regulator. The dynamic pressure regulator 57 can be implemented as a valve assembly that includes a proximal head portion 72, an intermediate body portion 74, and a distal actuator portion 76. The head portion 72 of the valve assembly can include an inlet 78 to receive the pressurized solvent stream and an outlet 80 through which the pressurized solvent stream is output such that the solvent stream flows through the head portion from the inlet 78 to the outlet 80. A seat 82 can be disposed within the head portion 72 and can include a bore 84 through which the solvent stream can flow from the inlet 78 to the outlet 80 of the head.

A needle 86 extends into the head portion 72 from the body portion 74 of the valve assembly through a seal 88. A position of the needle 86 can be controlled with respect to the seat 82 to selectively control a flow of the solvent stream from the inlet 78 to the outlet 80. In exemplary embodiments, the position of the needle 86 can be used to restrict the flow through the bore 84 of the seat 82 to increase the pressure of the system 10 and can selectively close the valve by fully engaging the seat 82 to interrupt the flow between the inlet 78 and the outlet 80. By controlling the flow of the solvent stream through the head portion based on the position of the needle 86, the pressure of the system 10 can be increased or decreased. For example, the pressure of the system 10 can generally increase as the needle 86 moves towards the seat 82 along the longitudinal axis L and can generally decrease as the needle 86 moves away from the seat 82 along the longitudinal axis L.

The actuator portion 76 can include an actuator 90, such as a solenoid, voice coil, and/or any other suitable electromechanical actuation device. In the present embodiment, the actuator 90 can be implemented using a solenoid having a main body 92 and a shaft 94. The shaft 94 can extend along the longitudinal axis L and can engage a distal end of the needle 86 such that the needle 86 and shaft can form a valve member. A position of the shaft 94 can be adjustable with respect to the main body 92 along the longitudinal axis L and can be controlled by a coil (not shown) of the main body 92, which generates a magnetic field that is proportional to an electric current passing through the coil and a load applied to the shaft. The electric current passing through the coil can be controlled in response to an actuator control signal received by the actuator 90. In some embodiments, the actuator control signal can be a pulse width modulated (PWM) signal and/or the actuator control signal can be determined, at least in part, by the feedback signal of the pressure transducer 59.

The position of the shaft 94 can be used to move the needle 86 towards or away from the seat 82 to increase or decrease pressure, respectively. In exemplary embodiments, a position of the shaft 94, and therefore a position of the needle 86 with respect to the seat 82 can be controlled and/or determined based on an amount of electric current flowing through the solenoid. For example, the greater the electrical current the closer to the needle 86 and shaft 94 are from the seat and the lower the pressure is in the system 10. The relationship between a position of the shaft 94 and the electric current flowing through the coil can be established through characterization of the actuator 90. The force imposed by the load on the solenoid can be proportional to the magnetic field. Similarly, the magnetic field can be proportional to the electric current flowing through the coil of the solenoid. For embodiments in which the actuator control signal is implemented as a PWM control signal, the pressure through the pressure regulator 57 (e.g., force balance between needle 86 and shaft 94) can be set by a correlation to the duty cycle of the PWM control signal, e.g., a percentage of the duty cycle corresponding to an "on" state.

The force imposed by the actuator 90 to set the pressure through the pressure regulator 57 can be manipulated for force control purposes by inclusion of a compressed spring 96. Spring 96 is compressed by collar 98 to apply a normalizing force to the actuator 90 through an exterior shaft liner 100. This normalizing force assists in providing a linear load force throughout the cycle of the actuator 90. In general, actuator 90 has a negative spring rate, such that shaft 94 when the actuator 90 is in an inactive state is forced in a direction opposite of outlet 80 (i.e., towards the end of the device labeled B), such that the force reduces as the solenoid stroke increases. To compensate for this force, compressed spring 96 applies a pressure to shaft 94 to counterbalance the negative spring rate of the actuator 90. In some embodiments, the spring rate selected for compressed spring 96 has a value that not only counterbalances but also applies a positive spring rate such that shaft 94 moves towards the end of the device labeled A.

To regulate pressure through device 57 from inlet 78 to outlet 80, the needle 86 and seat 82 are carefully positioned relative to one another. A calibrated position between the needle 86 and seat 82 is set at the position when the needle 86 first engages the bore 84 of the seat 82 to stop the flow of solvent. In general, care is taken to set this calibrated position, such that the needle 86 will not be jammed into the bore 84 during operation of pressure regulator 57. It is believed that prevention or at least minimization of the needle being jammed into the bore will extend the life of the pressure regulator and/or increase the working lifetime prior to a maintenance event.

During the lifetime of the pressure regulator 57, components, such as, for example the needle 86 or the seat 82 can become worn. These components may be replaced in maintenance events. After the maintenance event, the needle and seat need to be placed back into the calibration position.

Exemplary embodiments of the pressure regulator 57 include a calibration collar 110 secured to the shaft 94 to automatically (e.g., mechanically) reset the calibration position. That is, the calibration collar 110 applies a force on shaft 94 to lock further extension of the shaft 94. When the calibration collar 110 is secured onto shaft 94, a maintenance provider or user merely needs to position the shaft 94 in physical contact with the distal end of the needle and lock the calibration collar to mechanically set needle 86 relative to the seat 82 in the calibrated position.

To apply the force, the calibration collar 110 includes a spring 112 and two locking mechanisms 114 and 116. Locking mechanism 114 holds the calibration collar 110 to the exterior liner 100 of the shaft 94, whereas locking mechanism 116 grips the distal end 118 of the shaft 94 to clamp or lock the extended position of the shaft 94 to prevent jamming of the needle 86 into the seat 82. In the embodiment shown in FIG. 6, the locking mechanisms include fasteners 120 and 122 to secure a housing 124 forming the calibration collar 110 to the actuator 90.

During a maintenance event, the actuator 90 is inactivated (i.e., no signal is applied to drive the solenoid) and the flow of solvent is stopped. The needle 86 and seat 82 are in the calibrated position at the start of the maintenance event. That is, the needle 86 engages seat 82 to block bore 84. The calibration collar 110 attached to the shaft 94 as shown in FIG. 6 holds the needle and seat in this calibrated position. To obtain access to the distal end of the needle 86 and potentially to the seat, shaft 94 needs to be pulled back towards end B. In the calibration collar's configuration with both fasteners 120 and 122 secured, alignment of the needle 86, seat 82, and shaft 94 is maintained. However, to release this secured position, the user merely needs to loosen fastener 120 to release the grip of locking mechanism 116 from the distal end 118 of the shaft 94. The fastener 122 remains securely tightened or closed such that locking mechanism 114 continues to hold the housing 124 of the calibration collar 110 to the exterior liner 100. However, distal end 118 of the shaft 94 is free to move to allow access to the needle/seat for maintenance. At the conclusion of the maintenance event, the user places the proximal end 126 of the shaft 94 in contact with the needle 86 and tightens fastener 120 to reposition the needle 86 relative to the seat an in the calibrated position.

Figure 7A:
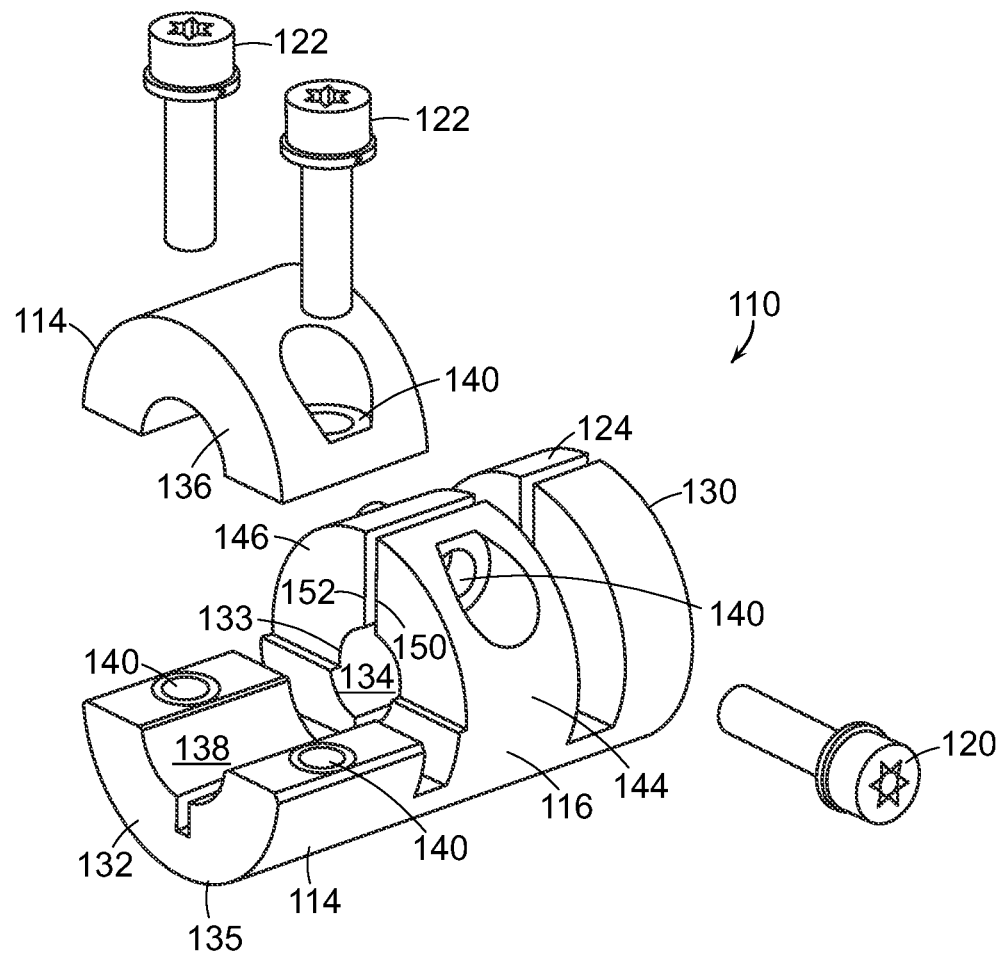
FIG. 7A is an exploded perspective view of an exemplary embodiment of a calibration collar according to the present disclosure.

FIG. 7A is an exploded view of calibration collar 110. In FIG. 7A, a portion of locking mechanism 114 (e.g., clamp 114) is shown in an unfastened state to show additional details of the interior of the calibration collar 110. The calibration collar 110 is formed from housing 124, typically manufactured from a metal, such as, for example, stainless steel or aluminum. The spring 112 (shown in FIG. 6 but not shown in FIG. 7A) is disposed at least partially within a first end 130 of the housing. Locking mechanism 114 is disposed on the opposite end or the second end 132 and between locking mechanism 114 and the first end 130 is locking mechanism 116 (e.g., clamp 116). The spring 112 preloads and automatically positions the needle 86 to the seat 92. In some embodiments in which the needle is manually positioned, spring 112 can be removed.

A channel 134 is defined within housing 124 and the size of channel 134 is configured to accept at least a portion (such as, for example the distal end 118 and a portion of the exterior liner 100) of the shaft 94. The locking mechanism 114 surrounds channel 134 and is sized to receive the exterior liner 100. The locking mechanism 114 includes a base portion 135 and a top portion 136. When fasteners 122 are installed and tightened within openings 140, the locking mechanism is configured to secure base portion 135 to top portion 136 in a locked position, in which the housing 124 is held to the exterior liner 100. In embodiments, surface 138 defining a wall of the channel through locking mechanism 114 can be textured to apply a frictional force to further secure the calibration collar 110 to the actuator 90. Applied textures can include raised bumps, ribs, or grooves.

Figure 7B:
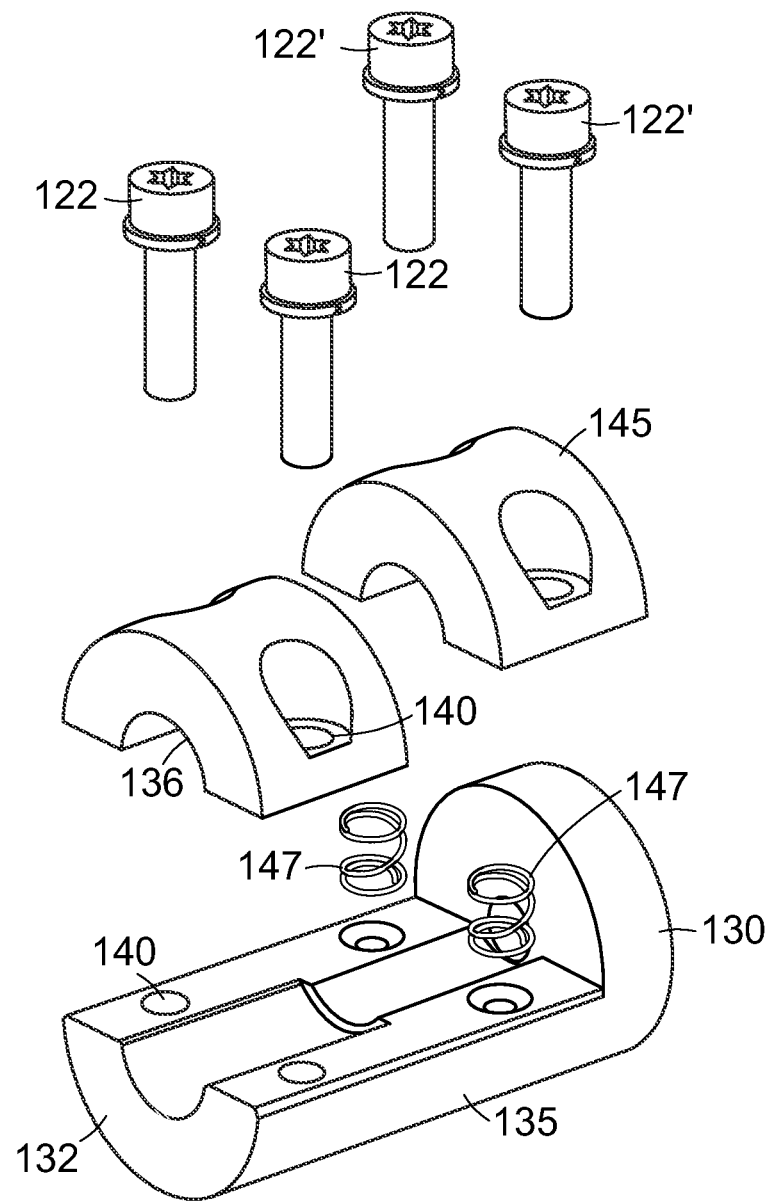
FIG. 7B is an exploded perspective view of another exemplary embodiment of a calibration collar according to the present disclosure.

Locking mechanism 116 is also shown in an unfastened state in FIG. 7A. Fastener 120 secures locking mechanism 116 in a closed position by forcing clamping portions 144 and 146 together at free ends 150 and 152. As shown in FIG. 7A, each of the clamping portions 144 and 146 are integrally formed with the housing. In addition, base portion 135 of locking mechanism 114 is also integrally formed with the housing. In another embodiment, clamping portions 144 and 146 can be replaced with a two piece design similar to that shown by base portion 135 and top portion 136. In this two-piece embodiment shown in FIG. 7B, fastener 120 as shown in the embodiment of FIG. 7A is replaced with two fasteners 122' and portions 144 and 146 as shown in the embodiment of FIG. 7A are replaced with a unitary piece 145 which is separate from base portion 135. Springs 147 can be used to aid in separating piece 145 when fasteners 122' are loosened or removed.

Figure 8:
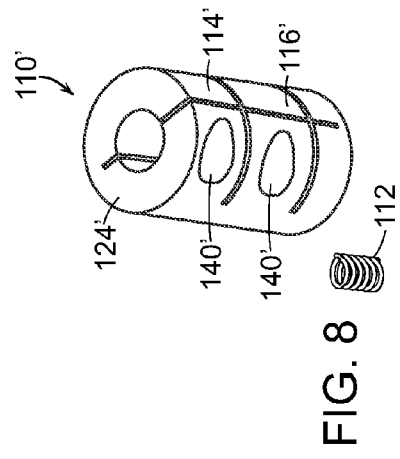
FIG. 8 is a perspective view of another exemplary embodiment of the calibration collar according to the present disclosure; in this view the calibration collar is shown without fasteners.
Figure 9:
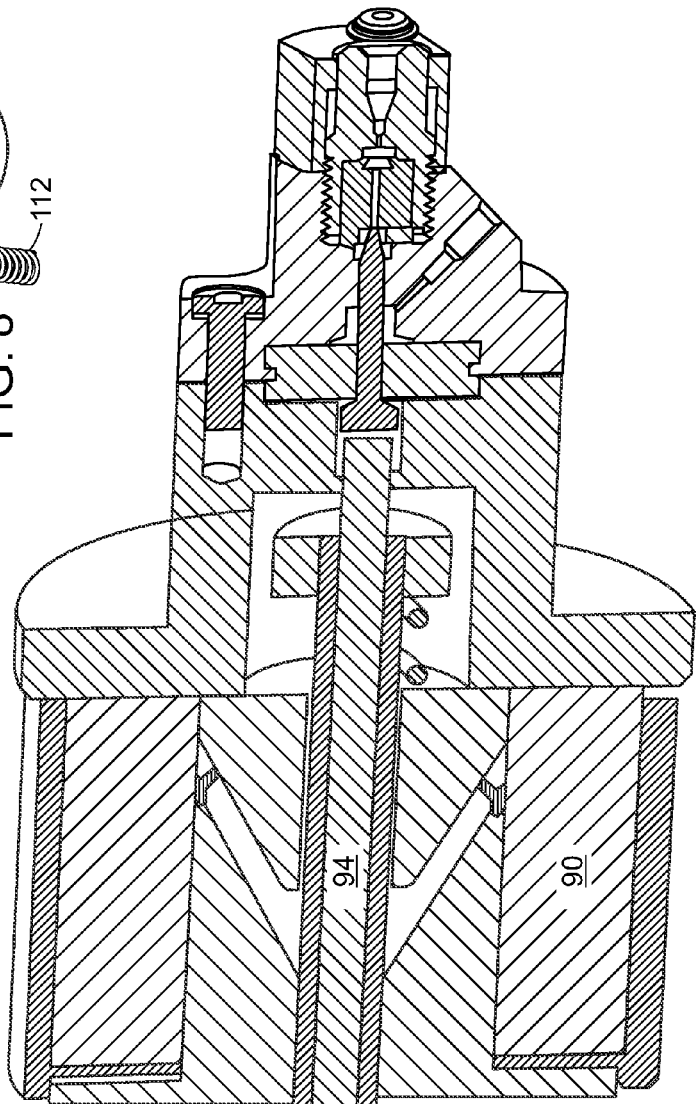
FIG. 9 is a cross-sectional view of another exemplary dynamic pressure regulator; in this view the dynamic pressure regulator includes the calibration collar of FIG. 8.

Locking mechanisms 114 and 116 can be implemented in numerous different configurations. For example, FIG. 8 shows an another calibration collar 110' with locking mechanisms 114' and 116' each of which are integrally formed with housing 124' and secured with a single fastener in each of openings 140'. A cross-sectional view of calibration collar 110' is shown in FIG. 9. In FIG. 9, calibration collar 110' is secured to actuator 90 through shaft 94 and exterior liner 100.

In other embodiments, figures not shown, the locking mechanism 114 and/or 116 can be electromechanical locking assemblies in which an applied electric signal is used to open and close the mechanisms.

FIGS. 10a and 10b show an exemplary embodiment of shaft 94. As shown in FIGS. 6 and 9, shaft 94 lies within exterior liner 100 and is the portion of the actuator 90 that contacts needle 86. The proximal end 126 of shaft 94, when in use for pressure regulation, contacts the needle 86 to apply a force to the needle to change its position. In embodiments, the distal end 118 of the shaft 94 is secured within one of the exemplary calibration collars disclosed herein. The exterior surface of the distal end 118 can include a texture, such as the texture shown in FIGS. 10a and 10b to provide further grip or friction between locking mechanism 116 and the distal end 118. In addition to the exterior surface of the distal end 118 being textured, the interior surface 133 of a wall defining the channel 134 through locking mechanism 116 can also be textured. Applied textures can include raised bumps, ribs, grooves, or the like.

Figure 11:
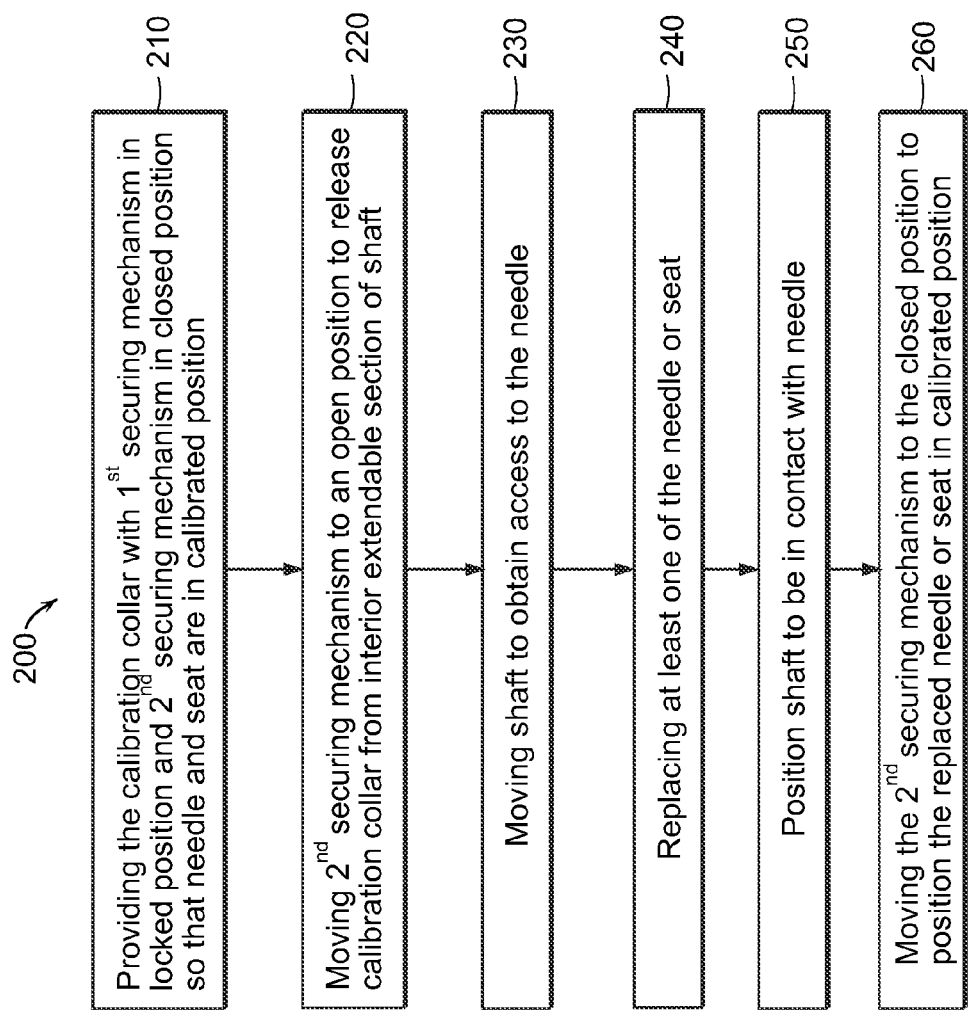
FIG. 11 is a flowchart illustrating an exemplary method of using the calibration collar of the present disclosure to maintain a calibrated position between a needle and a seat after a maintenance event.
Figure 12:
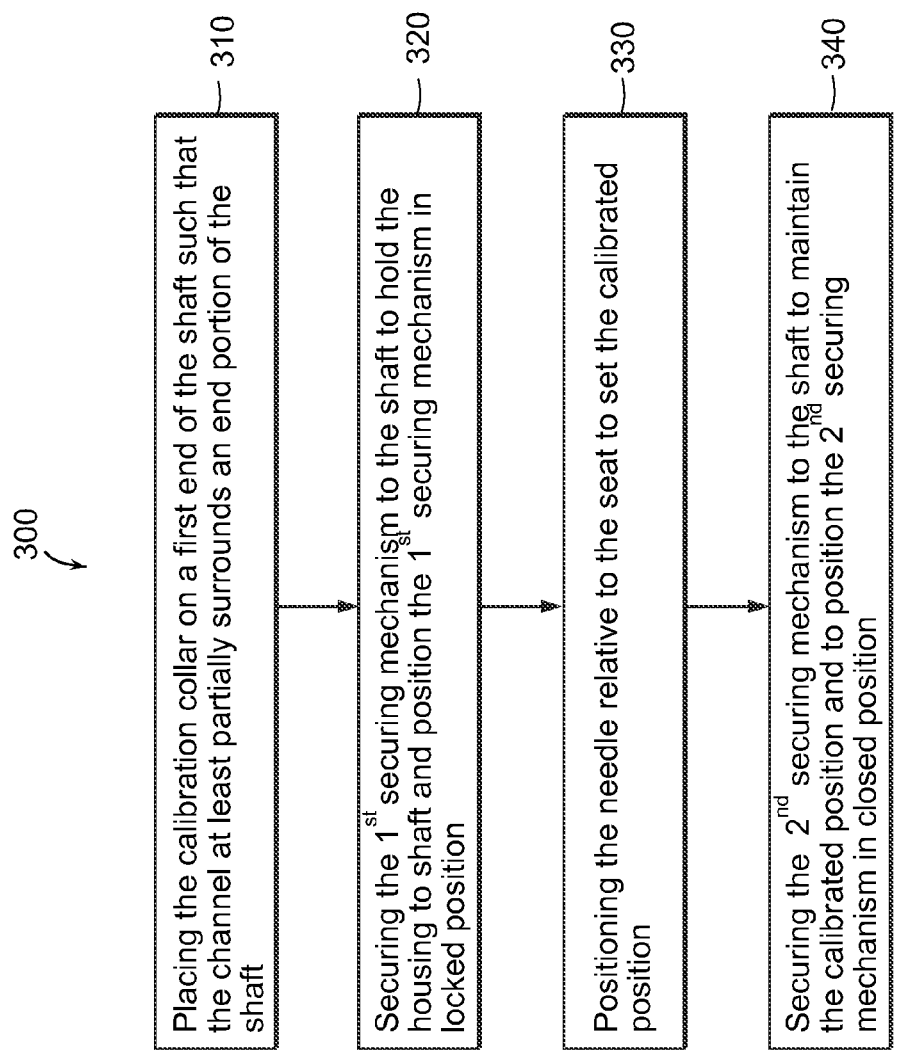
FIG. 12 is a flowchart illustrating an exemplary method of using the calibration collar to set and maintain a calibrated position between a needle and a seat in a pressurized flow system.

FIGS. 11 and 12 show flowcharts of methods in which the exemplary calibration collars of the present disclosure are utilized. FIG. 11 illustrates an exemplary method 200 of replacing a needle or a seat in a pressurized flow device, such as, for example a pressure regulator in a $CO_2$-based chromatography system. FIG. 12 illustrates an exemplary method 300 of setting and maintaining a calibrated position between a needle and a seat in a pressurized flow system, such as for example a $CO_2$-based chromatography system operated at or near supercritical conditions.

Referring to FIG. 11, method 200 includes the following steps: providing the calibration collar, such as, for example collar 110 or 110', with the first securing mechanism (e.g. locking mechanism) in the locked position and the second securing mechanism (e.g., locking mechanism) in the closed position to secure and grip the calibration collar to the shaft of the actuator so that the needle and seat are in a calibrated position—step 210; moving the second securing mechanism from the closed position (e.g., fastener tightened or secured) to an open position (e.g., fastener loosened or removed) to release the grip of the calibration collar from an interior extendable section of the shaft (e.g., shaft 94)—step 220; moving the shaft (e.g., proximal end of the shaft) to obtain access to the needle—step 230; replacing at least one of the needle 86 or the seat 82—step 240; positioning the shaft to be in physical contact with an end of the needle 86 or replaced needle—step 250; and moving the second securing mechanism from the open position to the closed position (e.g., tightening fastener or securing clamp through electromechanical means) to grip the interior extendable section of the shaft and position the replaced needle or seat in the calibrated position—step 260.

There are numerous advantages provided by the above method. For example, the method provides for consistent calibration between the needle and the seat after maintenance events or upon start-up of a dormant system. That is, the calibration collar 110, secured to the exterior liner 100 and the interior shaft 94 of the actuator 90 mechanically set the position of the needle relative to the seat such that the calibration position is consistently provided after each maintenance or start-up event. In addition, as locking mechanism 114 secures the calibration collar to the actuator 90 and locking mechanism 116 grips the shaft 94 to set and maintain the calibration position, a user's interaction with the calibration collar 110 and associated pressure regulator 57 after maintenance is complete is merely to tighten or secure locking mechanism 116. As a result, shut down time associated with maintenance events is minimized.

In addition to the above advantages, the method 200 in certain embodiments, can include features which improve efficiency and further limit a user's interaction. For example, method 200 can be implemented for use with one or more electromechanical locking assemblies used to secure or close locking mechanisms 114 and/or 116. Method 200, in these embodiments, can further including one or more of the following features. Release of the securing or locking mechanisms can occur automatedly without user input upon the actuator being placed in a non-operating position (e.g., no signal supplied to the actuator, no flow of solvent through the regulator). The locking mechanism 116 can move from the closed position to an open position automatically at each start-up event of the regulator 57—once again without user input. In addition, it is noted that step 250 occurs automatically when spring 112 is included in the calibration collar 110, which also includes locking mechanisms 114 and 116. In embodiments which do not include spring 112, a user would manually position the shaft to be in physical contact with an end of the needle 86 or replaced needle.

Referring to FIG. 12, method 300, a method of setting and maintaining a calibrated position between a needle and a seat in a pressurized flow system, is illustrated. Exemplary method 300 includes the steps of: placing the calibration collar, such as collar 110 on a first end of the shaft of an actuator such that the channel 134 defined in the housing 124 at least partially surrounds the distal end portion 118 of the shaft—step 310; securing the first securing mechanism (e.g., locking mechanism 114) of the calibration collar to the shaft to hold the housing 124 to the shaft 94 and to position the first securing mechanism in the locked position—step 320; positioning the needle 86 relative to the seat 82 to set the calibrated position (e.g., needle 86 first engages seat 82 to block bore 84)—step 330; positioning a second end of the shaft of the actuator to be in physical contact with the needle (e.g., placing the proximal end 126 of the shaft in contact with the distal end of the needle)—step 340; and securing the second securing mechanism (e.g. locking mechanism 116) of the calibration collar to the shaft to maintain the calibrated position and to position the second securing mechanism in the closed position—step 350. It is noted that step 330 occurs automatically when spring 112 is included in the calibration collar 110, which also includes locking mechanisms 114 and 116. In embodiments which do not include spring 112, a user would manually position the shaft to be in physical contact with an end of the needle 86 or replaced needle.

Method 300 can also additionally include steps to account for a maintenance event—such as, for example, a replacement of a needle or seat. These steps return the needle at the conclusion of the maintenance event to the calibration position—without the user having to manual reset or find the calibration position. Instead, the user merely tightens or closes the second securing mechanism after maintenance is complete to return the components of the regulator 57 to the calibrated position.

For example, method 300 can further include the following steps: moving the second securing mechanism from the closed position to an open position to release the grip of the calibration collar; moving the second end (e.g., proximal end 126) of the shaft to obtain access to the needle (e.g., to obtain access for a maintenance event); positioning the second end of the shaft to be in physical contact with the exposed end (e.g., distal end) of the needle; and moving the second securing mechanism from the open position to the closed position to grip the shaft and to return the needle and seat to the calibrated position.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the technology.

The invention claimed is:

1. A calibration collar for automatically setting a position of a needle to a seat in a pressurized flow system including an actuator positioned to drive the needle relative to the seat, the actuator comprising a shaft including an exterior liner and an interior extendable section, the calibration collar comprising:
   a housing including a first end and a second end, the housing defining a channel sized to accept at least a portion of the shaft of the actuator;
   a first securing mechanism positioned at the second end of the housing and surrounding the channel, the first securing mechanism, when in a locked position, holds the housing to the exterior liner of the shaft;
   a second securing mechanism, independent of the first securing mechanism, the second securing mechanism when in a closed position, grips at least a portion of an external perimeter surface of the interior extendable section of the shaft to clamp the housing to the shaft; and
   a spring disposed at least partially in the first end of the housing and extending into the channel to apply a known load on the shaft when the shaft is seated in the housing.

2. The calibration collar according to claim 1, wherein the first securing mechanism is a clamp.

3. The calibration collar according to claim 1, wherein the second securing mechanism is a clamp.

4. The calibration collar according to claim 1, wherein the second securing mechanism is positioned between the first securing mechanism and the first end of the housing.

5. The calibration collar according to claim 2, wherein the clamp comprises a base portion integrally formed with the housing and a top portion secured to the base portion with two fasteners.

6. The calibration collar according to claim 3, wherein the clamp comprises a base portion integrally formed with the housing and a top portion secured to the base portion with two fasteners.

7. The calibration collar according to claim 3, wherein the clamp comprises a first clamp portion integrally formed with the housing and having a first free end and a second clamp portion integrally formed with the housing and including a second free end, the second free end of the second clamp portion opposing the first free end of the first clamp portion, the first and second clamp portions being secured together with a fastener.

8. The calibration collar according to claim 1, wherein the housing is formed at least in part of stainless steel.

9. The calibration collar according to claim 1, wherein the housing is formed at least in part of aluminum.

10. The calibration collar according to claim 1, wherein at least a portion of a surface of the housing defining the channel is textured to facilitate gripping of at least a portion of an external perimeter surface of the interior extendable section of the shaft of the actuator when the second securing mechanism is in the closed position.

11. The calibration collar according to claim 10, wherein the texture applied comprises one or more of radial grooves, raised bumps, or raised ribs.

12. The calibration collar according to claim 1, wherein the second securing mechanism comprises a electromechanical locking assembly.

13. A method of replacing at least one of a needle or a seat in a pressurized flow device, the method comprising:
   providing the calibration collar of claim 1, with the first securing mechanism in the locked position and the second securing mechanism in the closed position to secure and grip the calibration collar to the shaft of the actuator in an operating position in which the needle and the seat are in a calibrated position;
   moving the second securing mechanism from the closed position to an open position to release the grip of the calibration collar from the interior extendable section of the shaft;
   moving the shaft to obtain access to the needle;
   replacing at least one of the needle or seat;
   positioning the shaft to be in physical contact with an end of the needle or a replacement needle; and
   moving the second securing mechanism from the open position to the closed position to grip the interior extendable section of the shaft and position the replaced needle or seat in the calibrated position.

14. The method of claim 13, wherein moving the second securing mechanism from the closed to the open position comprises releasing a clamping mechanism.

15. The method of claim 14, wherein releasing a clamping mechanism comprises loosening a fastener of the clamping mechanism.

16. The method of claim 14, wherein releasing a clamping mechanism comprises electromechanically releasing the clamping mechanism.

17. The method of claim 13, wherein moving the second securing mechanism from the open position to the closed position comprises activating a clamping mechanism.

18. The method of claim 17, wherein activating the clamping mechanism comprises tightening a fastener of the clamping mechanism.

19. The method of claim 17, wherein activating the clamping mechanism comprises electromechanically closing the clamping mechanism.

20. The method of claim 16, wherein releasing the clamping mechanism occurs automatedly without user input upon the actuator being placed in a non-operating position.

21. The method according to claim 20, wherein moving the second securing mechanism from the open position to the closed position occurs automatedly.

22. The method according to claim 13, wherein moving the second securing mechanism from the open position to the closed position occurs automatedly at each start-up event of the pressurized flow device.

23. A method of setting and maintaining a calibrated position between a needle and a seat in a pressurized flow system including an actuator positioned to drive the needle relative to the seat, the method comprising:
   placing the calibration collar of claim 1 on a first end of the shaft of the actuator such that the channel defined in the housing at least partially surrounds an end portion of the shaft;
   securing the first securing mechanism of the calibration collar to the shaft to hold the housing to the shaft and to position the first securing mechanism in the locked position;
   positioning the needle relative to the seat to set the calibrated position;
   positioning a second end of the shaft of the actuator to be in physical contact with an exposed end of the needle; and
   securing the second securing mechanism of the calibration collar to the shaft to grip the external perimeter surface of the extendable section of the shaft to maintain the calibrated position and to position the second securing mechanism in the closed position.

24. The method of claim 23, further comprising:
   moving the second securing mechanism from the closed position to an open position to release the grip of the calibration collar from the shaft;
   moving the second end of the shaft to obtain access to the needle;
   positioning the second end of the shaft to be in physical contact with the exposed end of the needle; and
   moving the second securing mechanism from the open position to the closed position to grip the shaft and to return the needle and the seat in the calibrated position.

25. The method of claim 23, wherein positioning the needle relative to the seat to set the calibrated position occurs automatically.

* * * * *